United States Patent
Hill et al.

(10) Patent No.: US 7,528,945 B2
(45) Date of Patent: *May 5, 2009

(54) METHOD TO DETERMINE THE OPTICAL QUALITY OF A GLAZING

(75) Inventors: Barry Raymond Hill, St Helens (GB); Simon Peter Aldred, Tarleton (GB)

(73) Assignee: Pilkington plc, St. Helens, Merseyside (GB)

( * ) Notice: Subject to any disclaimer, the term of this patent is extended or adjusted under 35 U.S.C. 154(b) by 210 days.

This patent is subject to a terminal disclaimer.

(21) Appl. No.: 10/548,661

(22) PCT Filed: Mar. 15, 2004

(86) PCT No.: PCT/GB2004/001063

§ 371 (c)(1),
(2), (4) Date: Sep. 9, 2005

(87) PCT Pub. No.: WO2004/083835

PCT Pub. Date: Sep. 30, 2004

(65) Prior Publication Data

US 2007/0036464 A1    Feb. 15, 2007

(30) Foreign Application Priority Data

Mar. 19, 2003  (GB) ................. 0306259.3

(51) Int. Cl.
*G01N 21/00* (2006.01)

(52) U.S. Cl. ................................. 356/239.1
(58) Field of Classification Search ............... 357/237.1
See application file for complete search history.

(56) References Cited

U.S. PATENT DOCUMENTS

| | | | | |
|---|---|---|---|---|
| 4,930,889 A * | 6/1990 | Van Donselaar et al. | . | 356/237.6 |
| 5,363,188 A * | 11/1994 | Didelot et al. | ........... | 356/124.5 |
| 5,583,904 A * | 12/1996 | Adams | ...................... | 378/22 |
| 5,694,479 A | 12/1997 | Guering et al. | | |
| 6,891,980 B2 * | 5/2005 | Gerhard et al. | .............. | 382/321 |
| 6,909,502 B2 * | 6/2005 | Capaldo et al. | .......... | 356/239.2 |
| 2003/0151739 A1 * | 8/2003 | Capaldo et al. | .......... | 356/239.1 |

OTHER PUBLICATIONS

Form PCT/ISA/210 (International Search Report dated Jul. 5, 2004).

* cited by examiner

*Primary Examiner*—Roy M Punnoose
*Assistant Examiner*—Isiaka O Akanbi
(74) *Attorney, Agent, or Firm*—Buchanan, Ingersoll & Rooney PC

(57) ABSTRACT

A method of determining the optical quality of a glazing which includes at least one area having a reduced light transmission, involves producing a shadowgraph image of the glazing and measuring the illumination of the glazing at a plurality of measurement points arranged in an array extending over the glazing. The deviation in illumination from a desired value at each measurement point is determined and the at least one area of reduced light transmission is omitted from the array of measurement points.

19 Claims, 2 Drawing Sheets

METHOD TO DETERMINE THE OPTICAL QUALITY OF A GLAZING

This application claims priority under 35 U.S.C. § 119 to British Application No. 0306259.3 filed on Mar. 19, 2003, and is a U.S. national phase application of International Application No. PCT/GB2004/1001063 filed on Mar. 15, 2004 which designates the United States, the entire contents of both of which are hereby incorporated by reference.

This invention relates to a method for determining the optical quality of glazings, in particular vehicle glazings.

In the production of vehicle glazings it is desirable to inspect every glazing to determine its optical quality, to ensure that it is acceptable for use as a vehicle glazing.

The use of shadowgraphs for evaluating the optical quality of glazings is well known. A glazing is positioned between a localised light source (a high intensity point source) and a shadowgraphic image of the glazing is projected onto a screen. The shadowgraph image is recorded by a CCD camera and analysed with the aid of a computer. The shadowgraph of a glazing is characterised by illumination variations which are related to the transmitted distortion of the glazing. The transmitted distortion of a glazing is caused by variations in the thickness of the glass. In the case of a laminated glazing these variations can be introduced during the manufacture of the glass plies, or may be introduced during the lamination process. The result is an effect called "wedge". Ideally, the faces of the glass plies are perfectly parallel so that after lamination the plies are retained parallel to each other. In practice, however, there are variations in the thickness of the individual glass plies and the laminate itself that produce shallow wedge shaped sections in the glass or laminated glazing which causes deflection of light resulting in optical distortion. Variation in this wedge angle causes transmitted light to converge or diverge and this is represented in the shadowgraph image by illumination variations. The more rapidly the wedge angle changes across the surface of the glass, the greater this convergence or divergence becomes.

U.S. Pat. No. 5,694,479 discloses a process for measuring the optical quality of a glazing which utilises shadowgraphs. A shadowgraph image of the glazing is recorded and processed such that point measurements are made of the illumination. The processed shadowgraph image is then used to construct a reference image and comparisons are then made between points of the processed image and corresponding points of the reference image. In constructing the reference image, it is first necessary to determine an illumination value for all measurement points of the recorded shadowgraph image, including the regions of the image corresponding to printed areas of the glazing. In these regions an illumination value is estimated by extrapolating from the known illumination values of adjacent measurement points. Once illumination values have been estimated for the measurement points on the shadowgraph image corresponding to the printed areas of the glazing, the reference image is constructed by carrying out convolution filtering over the entire shadowgraph image. Constructing the reference image in this way is time consuming and a number of calculations are carried out which are unnecessary.

It is an object of the present invention to improve on the aforementioned process.

According to the invention there is provided a method of determining the optical quality of a glazing which includes at least one area having a reduced light transmission comprising the following steps:

producing a shadowgraph image of the glazing;

measuring the illumination of the glazing at a plurality of measurement points arranged in an array extending over the glazing;

determining any deviation in illumination at those points from a desired value at each point;

wherein the at least one area of reduced light transmission is omitted from the array of measurement points.

The invention further provides a method to determine the optical quality of a glazing comprising the following steps:

illuminating the glazing with a localized light source to produce a shadowgraph image;

recording the shadowgraph image;

determining valid measurement points of the shadowgraph image which excludes those points which correspond to obscured areas of the glazing;

processing the recorded shadowgraph image to determine an illumination value for each valid measurement point;

constructing a reference image by scanning a convolution window point by point over the processed image and using a convolution filter to calculate a reference illumination value at points of the reference image which correspond to each point of the processed image by averaging the illumination values of the valid measurement points of the processed image covered by the convolution window;

comparing the illumination value of each valid measurement point of the processed shadowgraph image with corresponding points of the reference image to determine the optical quality of the glazing.

The method of the invention ignores the optical quality of the glazing in the areas in which it is obscured (e.g. a printed peripheral obscuration band, or a printed patch which conceals the base of a rear view mirror attached by adhesive), and hence only performs calculations which are necessary and reduces the amount of time required to determine the optical quality of the glazing.

In a preferred embodiment of the invention the convolution window is of constant area during the scanning operation.

The method preferably includes the step of recording the reference image for comparison with the processed image.

In the method a valid measurement point is preferably one in which the illumination value at that point is equal to or above a pre-set threshold.

In the method it is preferable that when the point of the convolution window for which the reference illumination is being calculated corresponds with a non-valid measurement point of the processed image, a reference illumination is not calculated.

In a preferred embodiment non-valid measurement points are not taken into account in the construction on the reference image.

Preferably the same light source is used for the production of the shadowgraph image and in relation to calculating the reference image.

An embodiment of the invention will now be described with reference to the drawings in which:—

Figure 1:
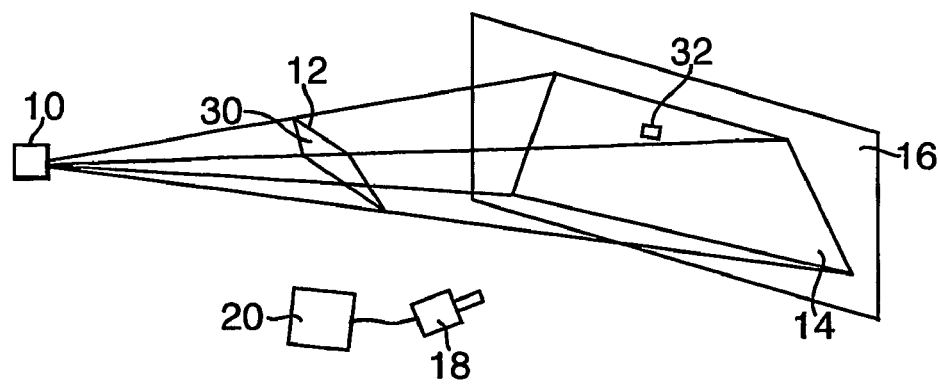
FIG. 1 shows a perspective view of the arrangement of apparatus for performing a preferred embodiment of the invention.

In FIG. 1, a localised light source 10 illuminates a windscreen 12 and produces a shadowgraph image 14 of the windscreen on screen 16. A printed patch 30 on the windscreen is shown which conceals the base of a rear view mirror attached to the windscreen with an adhesive. This patch casts a shadow 32 on the shadowgraph image 14. The light source is a 450 W Xenon arc lamp which provides a high intensity point source. The distance between the light source 10 and the windscreen 12 is 4 m and the distance between the windscreen 12 and the screen 16 is 2 m. In the case of windscreens it is preferable that the measurements are carried out under real conditions, and so the windscreen is observed at an angle similar to what it would be when fitted in a vehicle and the axis of the light source is horizontal and parallel to the axis of the vehicle. A CCD camera 18, for example a 10 bit area scan CCD camera with linear response such as Hitachi camera model number KP-F1, is also shown which records the shadowgraph image 14. Whilst the camera 18 is shown in FIG. 1 to be below the windscreen 12, this is not essential. It is only necessary that the camera has a non distorted view of screen 16 so that it can record the shadowgraph image 14. The CCD camera 18 is associated with a computer 20 which is used in determining the optical quality of the glazing. The shadowgraph image 14 recorded by the camera 18 is stored in the memory of computer 20 to aid in the construction of the reference image, and also for comparison with the reference image.

The shadowgraph image 14 is processed by the computer which detects valid and non-valid measurement points, where a valid measurement point corresponds to a non obscured part of the glazing and a non-valid measurement point corresponds to an obscured part of the glazing (e.g. a printed peripheral obscuration band, or a printed patch which conceals the base of a rear view mirror attached by adhesive). The valid measurement points are detected by the computer where the illumination value at that point is equal to or above a pre-set threshold and the non-valid measurement points are detected where the illumination value at that point is below the pre-set threshold. The shadowgraph image is then processed by quantifying the illumination values for each valid measurement point which is then stored in the computer memory. For each non-valid measurement point the illumination value is not quantified, but simply given a value of zero which is stored in the computer memory.

The processed image therefore consists of quantified point measurements of the illumination value of the recorded shadowgraph image for all measurement points except those points which correspond to obscured or printed areas of the glazing (i.e. the processed image comprises quantified point measurements of the illumination value of the valid measurement points). It is this processed image which is used to construct the reference image. This is done by "smoothing" the processed image by convolution filtering—scanning a convolution window point by point over the processed image and for each valid measurement point of the processed image a corresponding reference illumination value is calculated for the reference image by averaging the illumination values of the valid measurement points of the processed image covered by the convolution window.

Construction of the reference image by convolution filtering is straightforward in areas of the glazing in which the convolution window covers only valid measurement points of the processed image. However, where the convolution window covers at least one non-valid measurement point, adjustments need to be made.

Preferably a convolution window of dimensions 31×31 measurement points is used, but for illustrative purposes and with reference to FIG. 2, one of 3×3 measurement points will be used. FIG. 2, which is not to scale, shows part of the processed image which includes valid and non-valid measurement points shown as a grid, each measurement point being represented as a box. The convolution window is depicted by the boxes within the boundary marked 28 (of 3×3 boxes). The non-valid measurement points are shown as a solid block 32 and in this particular instance correspond to a printed patch 30 on the glazing which conceals the base of a rear view mirror attached to the windscreen with an adhesive. A convolution window 28 is shown at four successive positions during its scanning over the processed image, position 1 at FIG. 2A, position 2 at FIG. 2B, position 3 at FIG. 2C and position 4 at FIG. 2D. At each position during its scanning over the processed image, the arithmetic mean of the illumination values of the valid measurement points, is carried out. In FIG. 2 the dimensions of the convolution window is 3×3 and it is the geometric centre point of the window (shown as box 5) for which the reference illumination is being calculated.

Figure 2A:
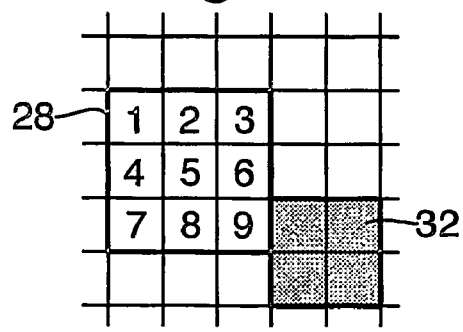
FIGS. 2A-2D show different positions of a convolution window as it scans part of a glazing in a method to construct a reference image according to a first embodiment of the invention.

In position 1 as shown in FIG. 2A the convolution filtering is straightforward as the convolution window covers only valid measurement points. To obtain the reference illumination value for the point of the reference image corresponding to the point of the processed image covered by box 5 of the convolution window, the following calculation is performed:

$$I_5 = \left[\sum_9^1 I\right]\bigg/9$$

i.e. the average of the actual illumination values of boxes 1 to 9 of the convolution window, each of which correspond to valid measurement points of the processed image.

Figure 2B:
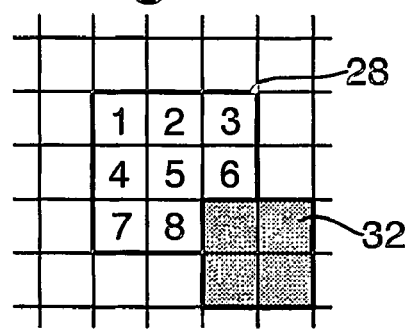

In position 2 as shown in FIG. 2B, the convolution window covers one non-valid measurement point of the processed image (corresponding to the point covered by box 9 of the convolution window). This point is ignored in calculating the reference illumination value for the point of the reference image corresponding to the point covered by box 5 of the convolution window, and the following calculation is performed to obtain the reference illumination value at that point:—

$$I_5 = \left[\sum_8^1 I\right]\bigg/8$$

i.e. the average of the actual illumination values of the boxes 1 to 8 of the convolution window, which correspond to valid measurement points of the processed image.

Figure 2C:
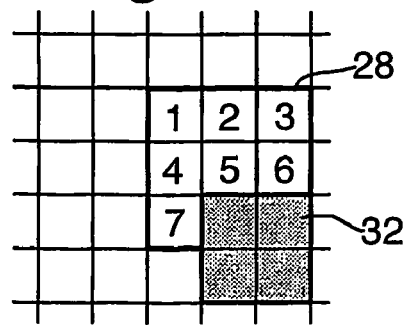

In position 3 as shown in FIG. 2C, the convolution window covers two non-valid measurement points of the processed image (corresponding to the points covered by boxes 8 and 9 of the convolution window) and these points are ignored in calculating the reference illumination value for the point of the reference image corresponding to the point covered by box 5 of the convolution window, and the following calculation is performed to obtain the reference illumination value at that point:—

$$I_5 = \left[\sum_7^1 I\right]/7$$

i.e. the average of the actual illumination values of boxes 1 to 7 of the convolution window, which correspond to valid measurement points of the processed image.

Figure 2D:
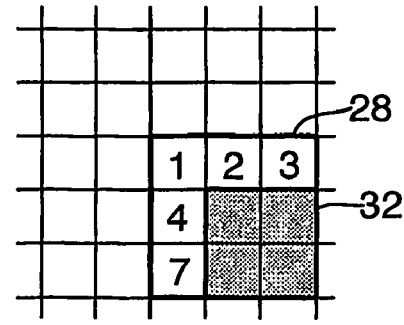

In the case where box 5 of the convolution window covers a non-valid measurement point of the processed image, such as the position shown in FIG. 2D, no reference illumination value is calculated and the corresponding point of the reference image is given a value of zero.

By performing convolution filtering as described above over the entire surface of the processed image, a reference image is constructed which comprises a reference illumination value for each corresponding valid measurement point of the processed image.

The reference image is now compared with the processed image to determine the optical quality of the glazing. The comparison is carried out by comparing the illumination values of corresponding points and calculating the ratio of illumination values of the points of the processed image to those of the reference image. In this way it is possible to determine defects in the glazing which can be compared with a specification, usually one provided by the vehicle manufacturer, to determine whether or not the glazing meets the required specification.

Figure 3A:
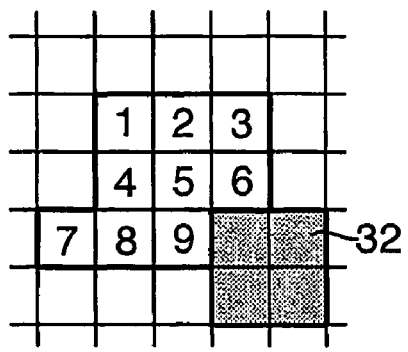
FIGS. 3A-3C show different positions of a convolution window as it scans part of a glazing in a method to construct a reference image according to a second embodiment of the invention.
Figure 3B:
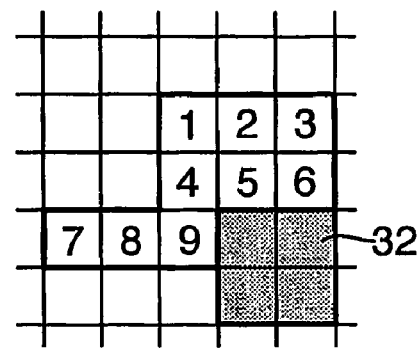
Figure 3C:
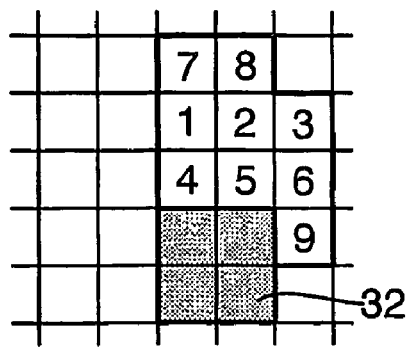

In the above method described with reference to FIG. 2, the convolution window effectively reduces in size when calculating a reference illumination value when the window scans over at least one non-valid measurement point of the processed image. For example in FIG. 2A the area is 9 boxes, in 2B it is effectively 8 boxes and in FIG. 2C it is effectively 7 boxes. This is because when the window covers boxes which correspond to non-valid measurement points of the processed image, these boxes are not taken into account in calculating the reference illumination value. In an alternative method, the convolution window may have a constant area during the scanning operation throughout entire construction of the reference image, i.e. when it scans over valid measurement points only of the processed image and also when it scans over non-valid measurement points of the processed image. This is done by altering the shape of the convolution window so that when it does cover a non-valid measurement point of the processed image, that non valid measurement point is ignored and replaced by a valid measurement point adjacent to the convolution window. In such a method the point of the convolution window at which the reference illumination is to be calculated may not always be the geometric centre point of the window, but is a predetermined point of the convolution window. This method is illustrated in FIG. 3, and in this particular example box 5 has been selected as the point of the convolution window at which the reference illumination is to be calculated, although a different box could be selected. The reference illumination calculated by this method for the point of the reference image corresponding to the point of the processed image covered by box 5 in each of the positions shown in FIGS. 3A-C is:—

$$I_5 = \left[\sum_9^1 I\right]/9$$

In each example illustrated in FIG. 3, the area of the convolution window is 9 boxes although in each case the window is not a 3×3 square of boxes.

As before with reference to the method described with reference to FIG. 2, a reference image is constructed by performing convolution filtering over the entire surface of the processed image, and the reference image comprises a reference illumination value for each corresponding valid measurement point of the processed image. The reference image is now, as before with reference to the method described with reference to FIG. 2, compared with the processed image to determine the optical quality of the glazing by comparing the illumination values of corresponding points and calculating the ratio of illumination values of the points of the processed image to those of the reference image. The defects in the glazing are thus determined and compared with a specification, usually one provided by the vehicle manufacturer, to determine whether or not the glazing meets the required specification.

In the above embodiments the same light source is used for the production of the shadowgraph image and in relation to calculating the reference image. This reduces errors which may be generated if different light sources are used It will be appreciated that the dimensions of each measurement point are smaller than the areas of the glazing which have a reduced light transmission, e.g. the printed patch 30 or a peripheral obscuration band. In the foregoing embodiments each measurement point has the dimensions of a pixel of the shadowgraph image which corresponds to a single sensing element of the CCD camera.

The invention claimed is:

1. A method of determining the optical quality of a glazing which includes at least one area having a reduced light transmission comprising the following steps:
    producing a shadowgraph image of the glazing;
    measuring the illumination of the glazing at a plurality of measurement points arranged in an array extending over the glazing;
    determining any deviation in illumination at those points from a desired value at each point;
    omitting from the array of measurement points the at least one area of reduced light transmission and ignoring the optical quality of the glazing in the area of reduced light transmission.

2. A method to determine the optical quality of a glazing comprising the following steps:
    illuminating the glazing with a localized light source to produce a shadowgraph image;
    recording the shadowgraph image;
    determining valid measurement points of the shadowgraph image which excludes those points which correspond to obscured areas of the glazing;
    processing the recorded shadowgraph image to determine an illumination value for each valid measurement point;
    constructing a reference image by scanning a convolution window point by point over the processed image and using a convolution filter to calculate a reference illumination value at points of the reference image which correspond to each point of the processed image by averaging the illumination values of the valid measurement points of the processed image covered by the convolution window;

comparing the illumination value of each valid measurement point of the processed shadowgraph image with corresponding points of the reference image to determine the optical quality of the glazing while ignoring the optical quality of the glazing in the obscured areas of the glazing.

3. A method as claimed in claim 2 wherein the convolution window is of constant area during the scanning operation.

4. A method as claimed in claim 3 including the step of recording the reference image for comparison with the processed image.

5. A method as claimed in claim 3, wherein a valid measurement point is one in which the illumination value at that point is equal to or above a pre-set threshold.

6. A method as claimed in claim 3 wherein when the point of the convolution window for which the reference illumination is being calculated corresponds with a non-valid measurement point of the processed image, a reference illumination is not calculated.

7. A method as claimed in claim 3 wherein non-valid measurement points are not taken into account in the construction on the reference image.

8. A method as claimed in claim 2 including the step of recording the reference image for comparison with the processed image.

9. A method as claimed in claim 8, wherein a valid measurement point is one in which the illumination value at that point is equal to or above a pre-set threshold.

10. A method as claimed in claim 8 wherein when the point of the convolution window for which the reference illumination is being calculated corresponds with a non-valid measurement point of the processed image, a reference illumination is not calculated.

11. A method as claimed in claim 8 wherein non-valid measurement points are not taken into account in the construction on the reference image.

12. A method as claimed in claim 2 wherein a valid measurement point is one in which the illumination value at that point is equal to or above a pre-set threshold.

13. A method as claimed in claim 12 wherein when the point of the convolution window for which the reference illumination is being calculated corresponds with a non-valid measurement point of the processed image, a reference illumination is not calculated.

14. A method as claimed in claim 12 wherein non-valid measurement points are not taken into account in the construction on the reference image.

15. A method as claimed in claim 2 wherein when the point of the convolution window for which the reference illumination is being calculated corresponds with a non-valid measurement point of the processed image, a reference illumination is not calculated.

16. A method as claimed in claim 15 wherein non-valid measurement points are not taken into account in the construction on the reference image.

17. A method as claimed in claim 2 wherein non-valid measurement points are not taken into account in the construction on the reference image.

18. A method as claimed in claim 2 wherein the same light source is used for the production of the shadowgraph image and in relation to calculating the reference image.

19. A method as claimed in claim 2 further comprising quantifying an illumination value for each valid measurement point and storing the illumination value for each valid measurement point in a computer, and assigning each non-valid measurement point an illumination value of zero which is also stored in the computer.

* * * * *